US011478488B2

(12) United States Patent
Plata-Salaman et al.

(10) Patent No.: US 11,478,488 B2
(45) Date of Patent: *Oct. 25, 2022

(54) CO-CRYSTALS OF TRAMADOL AND COXIBS

(71) Applicant: ESTEVE PHARMACEUTICALS, S.A., Barcelona (ES)

(72) Inventors: Carlos-Ramón Plata-Salaman, Barcelona (ES); Nicolas Tesson, L'Hospitalet de Llobregat (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/720,574

(22) Filed: Dec. 19, 2019

(65) Prior Publication Data
US 2020/0171055 A1 Jun. 4, 2020

Related U.S. Application Data

(63) Continuation of application No. 16/275,437, filed on Feb. 14, 2019, now Pat. No. 10,548,909, which is a continuation of application No. 15/231,915, filed on Aug. 9, 2016, now Pat. No. 10,245,276, which is a continuation of application No. 14/665,055, filed on Mar. 23, 2015, now abandoned, which is a continuation of application No. 14/066,127, filed on Oct. 29, 2013, now Pat. No. 9,012,440, which is a continuation of application No. 13/395,021, filed as application No. PCT/EP2010/002385 on Apr. 19, 2010, now Pat. No. 8,598,152.

(30) Foreign Application Priority Data

Oct. 16, 2009 (WO) ................. PCT/EP2009/007451

(51) Int. Cl.
A61K 31/635 (2006.01)
C07C 59/64 (2006.01)
C07C 217/74 (2006.01)
A61K 31/135 (2006.01)
A61K 31/192 (2006.01)
A61K 31/137 (2006.01)
A61K 9/16 (2006.01)
A61K 45/06 (2006.01)
C07D 231/12 (2006.01)

(52) U.S. Cl.
CPC .............. A61K 31/635 (2013.01); A61K 9/16 (2013.01); A61K 31/135 (2013.01); A61K 31/137 (2013.01); A61K 31/192 (2013.01); A61K 45/06 (2013.01); C07C 59/64 (2013.01); C07C 217/74 (2013.01); C07D 231/12 (2013.01); C07B 2200/13 (2013.01); C07C 2601/14 (2017.05)

(58) Field of Classification Search
CPC .............. A61K 31/135; A61K 2300/00; A61K 31/192; A61K 31/635; A61K 45/06; C07C 59/64; C07C 217/74; C07C 2601/14; C07D 231/12
See application file for complete search history.

(56) References Cited

U.S. PATENT DOCUMENTS

| 3,652,589 | A | 3/1972 | Flick |
| 5,466,823 | A | 11/1995 | Talley |
| 5,474,995 | A | 12/1995 | Ducharme |
| 5,516,803 | A | 5/1996 | Raffa |
| 5,633,272 | A | 5/1997 | Talley |
| 5,861,419 | A | 1/1999 | Dube |
| 5,932,598 | A | 8/1999 | Talley |
| 6,310,099 | B1 | 10/2001 | Fujimoto |
| 6,558,701 | B2 | 5/2003 | Bartholomaeus |
| 8,569,271 | B2 | 10/2013 | Salido |
| 8,598,152 | B2 | 12/2013 | Salaman |
| 8,846,744 | B2 | 9/2014 | Ranzani |
| 9,012,440 | B2 | 4/2015 | Salaman |
| 9,393,220 | B2 | 7/2016 | Bushmann |
| 10,238,668 | B2 | 3/2019 | Plata Salaman et al. |
| 10,245,276 | B2 * | 4/2019 | Plata Salaman ......... A61K 9/16 |
| 10,548,909 | B2 * | 2/2020 | Plata Salaman ........ A61P 19/00 |
| 2003/0147948 | A1 | 8/2003 | Shinoda |
| 2004/0076669 | A1 | 4/2004 | Bartholomaus |
| 2005/0090517 | A1 | 4/2005 | Norris |
| 2006/0172006 | A1 | 8/2006 | Lenaerts |
| 2007/0015841 | A1 | 1/2007 | Tawa |

(Continued)

FOREIGN PATENT DOCUMENTS

| CN | 1404826 A | 3/2003 |
| EP | 0546676 | 6/1993 |

(Continued)

OTHER PUBLICATIONS

Arora, Kapildev, K., et al., "Pharmaceutical co-crystals: a new opportunity in pharmaceutical science for a long-known but little-studied class of compounds", Polymorphism in Pharmaceutical Solids, Chapter 8, 2009, pp. 282-317/.
Brennan, et al., "Characterization of a rat model of incisional pain", Elsevier Science, B.V. Pain, 64, 1996, pp. 493-501.
Burke, D., et al., "Chirality: a blueprint for the future", British Journal of Anesthesia, 88(4), 2002, pp. 563-576.
Caira, "Crystalline polymorphism of organic compounds", Topics in Current Chemistry, vol. 198, 1998, pp. 163-208.
Chandran, et al., "Pharmacological modulation of movement-evoked pain in a rat model of osteoarthritis", European Journal of Pharmacology, Elsevier, VB. NL, vol. 613, No. 1-3, Jun. 24, 2009, pp. 38-45.

(Continued)

Primary Examiner — Jeffrey S Lundgren
Assistant Examiner — William Y Lee
(74) Attorney, Agent, or Firm — Hueschen and Sage

(57) ABSTRACT

The present invention relates to co-crystals of tramadol and co-crystal formers selected from NSAIDs/coxibs, processes for preparation of the same and their uses as medicaments or in pharmaceutical formulations, more particularly for the treatment of pain.

6 Claims, 9 Drawing Sheets

(56) References Cited

U.S. PATENT DOCUMENTS

| | | |
|---|---|---|
| 2007/0026078 A1 | 2/2007 | Almarsson |
| 2007/0141144 A1 | 6/2007 | Roberts |
| 2008/0031950 A1 | 2/2008 | Sesha |
| 2020/0360306 A1* | 11/2020 | Encina Garc a ..... A61K 31/135 |

FOREIGN PATENT DOCUMENTS

| | | |
|---|---|---|
| EP | 2022778 | 2/2009 |
| WO | WO1993004675 | 3/1993 |
| WO | WO1995000501 | 1/1995 |
| WO | WO1995015316 | 6/1995 |
| WO | WO1997014691 | 4/1997 |
| WO | WO1997038986 | 10/1997 |
| WO | WO1998003484 | 1/1998 |
| WO | WO1999011605 | 3/1999 |
| WO | WO1999013799 | 3/1999 |
| WO | WO2000051685 | 9/2000 |
| WO | WO2004078163 | 9/2004 |
| WO | WO2005055983 | 6/2005 |
| WO | WO2008064854 | 6/2008 |
| WO | WO2008085674 | 7/2008 |
| WO | WO2009018959 | 2/2009 |
| WO | WO20090143295 | 11/2009 |
| WO | WO2010028132 | 3/2010 |
| WO | WO2011044962 | 4/2011 |

OTHER PUBLICATIONS

Chou, T., "Theoretical basis, experimental design, and computerized simulation of synergism and antagonism in drug combination studies", Pharmacol Rev, 58, 2006, pp. 621-681.

Chu, et al., "Predicting aqueous solubility: the role of cyrstallinity". Current Drug Metabolism, 10, 2009, pp. 1184-1191.

Desiraju, "Crystal and co-crystal", The Royal Society of Chemisty CrystEngComm., 5(82), 2003, pp. 466-467.

Dirig, et al., "Characterization of variables defining hindpaw withdrawal latency evoked by radiant thermal stimuli", Elsevier, Journal of Neuroscience Methods, 76, 1997, pp. 183-191.

Dirig, et al., "Effect of cox-1 and cox-2 inhibition on induction and maintenance of carrageenan-evoked thermal hyperalgesia in rats", The Journal of Pharmacology and Experimental Therapeutics, The American Society for Pharmacology and Experimental Therapeutics, vol. 285, No. 3, 1998, pp. 1031-1038.

Dunitz, Crystal and co-crystal: a second opinion, The Royal Society of Chemistry, CrystEngComm, 5(91), 2003, pp. 506.

Emkey, et al., "Efficacy and safety of tramadol/acetaminophen tablets (Ultracet) as add-on therapy for osteoarthritis pain in subjects receiving a COX-2 nonsteroidal anti-inflammatory drug: a multicenter, randomized, double-blind, placebo-controlied trial", J. Rheumatol, 31(1), Jan. 2004, pp. 150-156.

Evans, et al., "Development of highly efficient resolutions of racemic tramadol using mandelic acid", Organic Process Research and Development, vol. 6, Jan. 1, 2002, pp. 729-737.

Giron, D., "Thermal analysis and calorimetric methods in the characterisation of polymorphs and solvates", Thermochimica Acta, 248, 1995, pp. 1-59.

Goldenberg, "Celecoxib, a selective cyclooxygenase-2-inhibitor for the treatment of rheumatoid arthritis and osteoarthritis", Clin. Ther., 21, 1999, pp. 1497-1513.

Hersh, et al., "Adverse drug interactions involving common prescription and over-the-counter analgesic agents", Clinical Therapeutics, Excerpta Medica, vol. 29, No. 11, Jan. 1, 2007, pp. 2477-2497.

International Search Report for PCT/EP2010/002385 dated Jul. 7, 2010.

Jaffe, J., "The Pharmacological basis of therapeutics", Goodman and Gilman's, 8th Edition, Chapter 22, 1190, pp. 522-573.

Jones, et al., "Pharmaceutical cocrystals: an emerging approach to physical property enhancement", MRS Bulletin, vol. 31, Nov. 2006, pp. 875-879.

Lv Yuandong, et al., "Application of celecoxib and tramadol in reducing pain from augmentation mammaplasty", Chin J. Aesth Plastic Surg, 19(4), 2008, pp. 280-282.

Macrae, et al., "Mercury CDS 2.0—new features for the visualization and investigation of crystal structures", Journal of Applied Crystallography, 41, 2008, pp. 466-470.

Ofoegbu, R.O., "Report on clinical trial with tramadol hydrochloride (Tramal) in the prevention of post-operative pain", Cure Ther Res, 36(3), 1984, pp. 436-444.

Paulson, et al., "Pharmacokinetics of celecoxib after oral administration in dogs and humans: effect of food and site of absorption", Journal of Pharmacology and Experimental Therapeutics, 297(2), May 2001, pp. 638-645.

Remenar, Julius, F., et al., "Celecoxib: nicotinamide dissociation: using excipients to capture the cocrystal's potential", Molecular Pharmaceutics, American Chemical Society, vol. 4, No. 3, May 1, 2007, pp. 386-400.

Shang, N., et al., "The role of cocrystals in pharmaceutical science", Drug Discovery Today, Elsevier, vol. 13, No. 9, May 1, 2008, pp. 440-446.

STN Registration No. 2204-53-I entered Nov. 16, 1984.

STN Registration No. 26159-34-2 entered Nov. 16, 1984.

Tallarida, et al., "Statistical Analysis of drug-drug and site-site interactions with isobolograms", Life Sciences, vol. 45, 1989, pp. 947-961.

Trask, Av, "An overview of pharmaceutical cocrystals as intellectual property", Molecular Pharmaceutics, American Chemical Society, vol. 4, No. 3. Jan. 1, 2007, pp. 301-309.

Vishweshwar, Journal of Pharmaceutical Sciences, vol. 95, 2006, pp. 499-516.

Wells, et al., Pharmacotherapy Handbok, 7th Edition, McGraw-Hill, 2009, pp. 12, 14, and 17.

Zaworotko, "Molecules to crystals, crystals to molecules . . . and back again?", American Chemical Society, Crystal Growth & Design, vol. 7, No. 1, 2007, pp. 4-9.

U.S. Appl. No. 17/609,452, Esteve Pharmaceuticals, S.A.

* cited by examiner

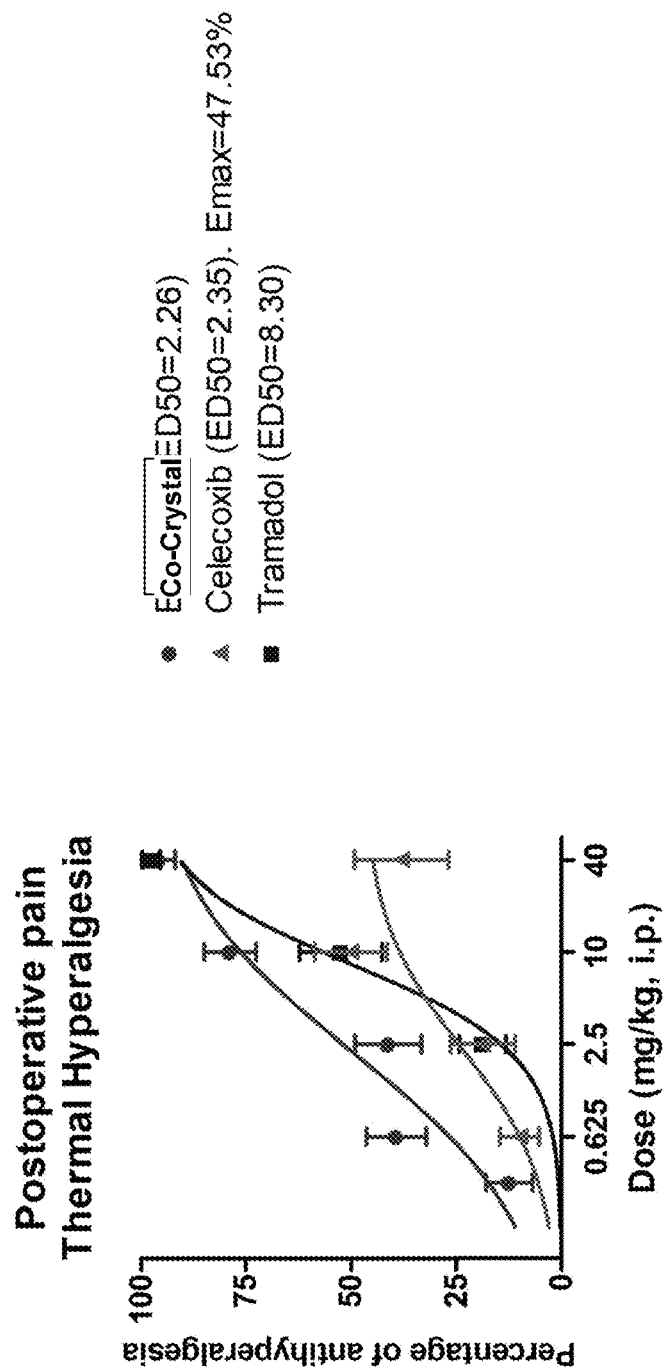
Fig. 8)

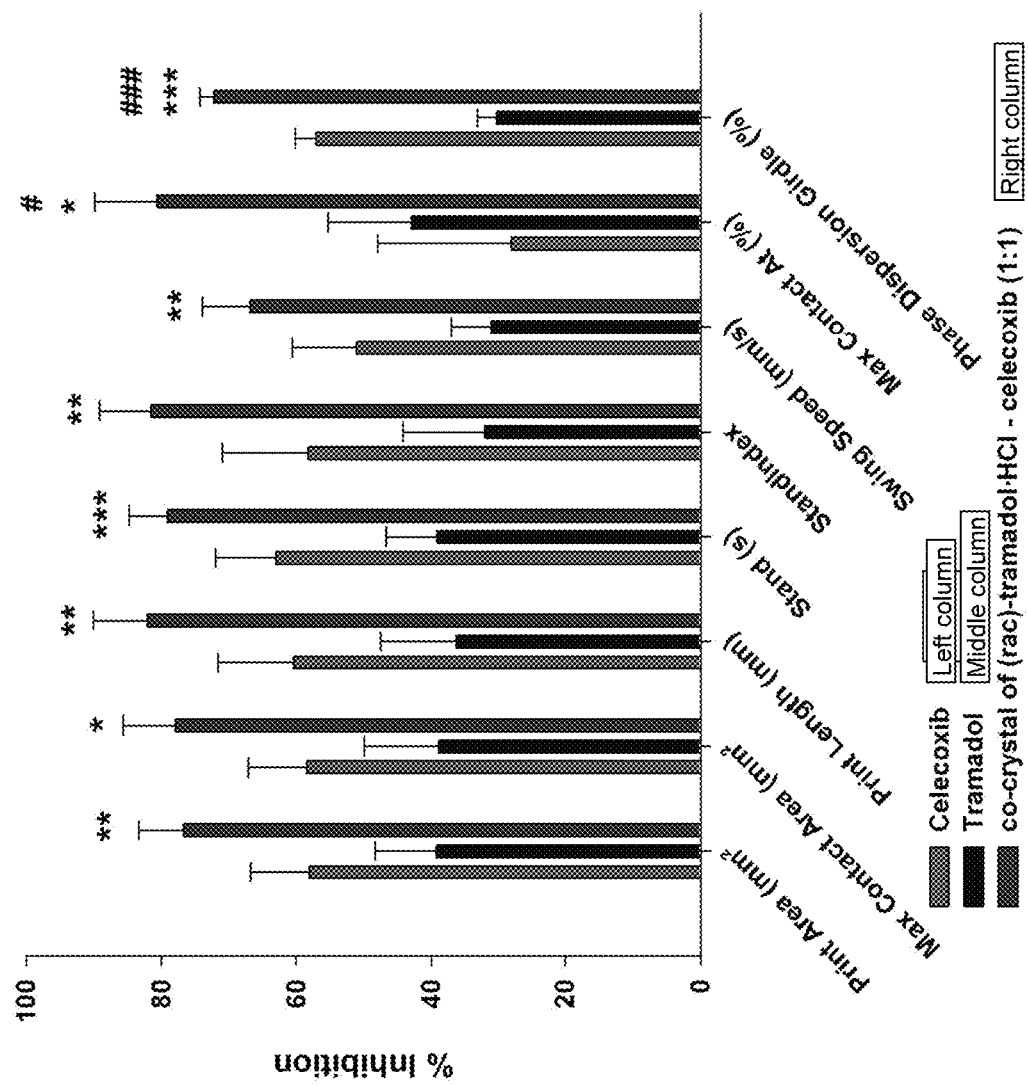
Fig. 9)

CO-CRYSTALS OF TRAMADOL AND COXIBS

The present invention relates to co-crystals of tramadol and NSAIDs—like coxibs—, processes for preparation of the same and their uses as medicaments or in pharmaceutical formulations, more particularly for the treatment of pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine.

There are many drugs that are known to be useful in the treatment or management of pain. Opioids are frequently used as analgesics in pain. Derivatives of morphine are indicated for the treatment of moderate to acute pain in human. The analgesic effect is obtained through their action on morphinic receptors, preferably the p-receptors. Among these derivatives of morphine, may be mentioned morphine, codeine, pethidine, dextropropoxyphenemethadone, lenefopan and others.

One of the morphinic derivatives that has shown very good results when orally administrated, and which is extensively marketed, is Tramadol, also available as a physiologically acceptable salt, particularly as a chlorohydrate. Tramadol, whose chemical name is 2-(dimethylaminomethyl)-1-(3-methoxyphenyl)cyclohexanol, has the following formula:

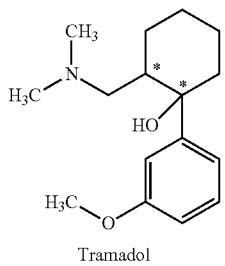 [SMILES: COc1cccc(C2(O)CCCCC2CN(C)C)c1]

Tramadol

This structure shows two different chiral centers and thus may exist in different diastereoisomers among which the tramadol is the cis-diastereisomer: (1R, 2R), or (1S, 2S), both also known as (+)-tramadol and (−)-tramadol and both of which contribute in different ways to its activity.

From the art it appears that this compound is neither fully opioid-like, nor non-opioid-like. Some studies have demonstrate that tramadol is an opioid agonist, whereas clinical experience indicates that it lacks many of the typical side effects of opioids agonist, for example respiratory depression, constipation or tolerance.

Due to their drawbacks, opioids cannot always be given repeatedly or at higher doses as analgesics to treat pain. The side effects of opioids are known in the art including e.g. J. Jaffe in "Goodman and Gilman's, The Pharmacological Basis of Therapeutics", 8$^{th}$ edition; Gilman et al.; Pergamon Press, New York, 1990, Chapter 22, pages 522-573.

Consequently it has been proposed to combine opioids with other drugs that are not opioid analgesic agents, in order to lower the amount of opioids needed to produce an equivalent degree of analgesia. Among these combinations, the association of tramadol with nonsteroidal anti-inflammatory drugs (NSAIDs) has been reported to be of particular interest (EP-0 546 676).

Thus it was the objective of the current invention to provide new means of improving the properties of tramadol, especially in regard to the treatment of pain, by providing new drugable forms of tramadol.

Especially desirable improvements/advantages of the new drugable form would include:
  improvement of physicochemical properties in order to facilitate the formulation, the manufacture, or to enhance the absorption and/or the bioavailability:
  thus
  being more active when compared to tramadol base or hydrochloride salt; or
  providing a form of tramadol with a further active agent having a beneficial pharmacological effect in itself, thus allowing for a highly efficient dose/weight relation of the final active principle or even
  allowing the use of a lower therapeutic dose of either tramadol and the further active agent, an NSAID—the coxib—, or of both;
  having a synergistic effect through the combination of tramadol and the further active agent, an NSAID—the coxib—, in the same new drugable form; or
  further
  having the bitter taste of tramadol removed or ameliorated;
  being easily obtainable, easy to manufacture or
  allowing more flexibility in formulating, or facilitating its formulation,
  being highly soluble, thus allowing better dissolution rates, especially if dissolving in an aqueous physiological surrounding, or
  improving stability of the co-crystal in comparison to the physical mixture of Tramadol/Active Agent (an NSAID—the coxib—) at the same ratio;
  allowing new routes of administration;
  also
  allowing—if necessary—to combine tramadol with a chemically usually non-compatible active agent in the same formulation or even in immediate contact, without having to isolate tramadol;
  or finally
  minimizing/reducing the side effects, especially the severe side effects, assigned to tramadol.

Other desirable improvements/advantages of the new drugable form would include being active in diseases or symptoms being or related to pain and its subtypes, especially those in which current treatment is insufficient like sciatica or frozen shoulder or pain related to central sensitization (central pain syndrome).

Most desirably the new drugable forms should combine more than one, most of these advantages.

This objective was achieved by providing new co-crystals of tramadol. It was found that tramadol was able to form co-crystals with NSAIDs—like coxib—, especially with celecoxib. These co-crystals show improved properties if compared to tramadol alone, and also good analgesic activity. The co-crystals thus obtained have a specific stoichiometry. Under the proper circumstance this is also another advantage of these new solid drugable forms possibly achieving some modulation of the pharmacological effects. While APIs (Active Pharmaceutical Ingredients) like tramadol in general have been recognized to form crystalline polymorphs, solvates, hydrates and amorphous forms for a number of years, there is little knowledge about which APIs will form co-crystals. Co-crystals are a specific type of crystalline form which provide a new avenue to modulate the API form and thus to modulate API properties. Co-crystals contain an API and at least one other component which crystallize together. Selection of the other component helps determine whether a co-crystal will form and what properties the co-crystal will have. Just as a polymorph, solvate, hydrate or amorphous form of an API can modulate stability, solubility, and hygroscopicity, a co-crystal can modulate those same properties.

Thus the main object of the present invention is a co-crystal comprising tramadol either as a free base or as a physiologically acceptable salt and at least one NSAID/coxib.

The coxibs are highly interesting NSAIDs for being the co-crystal former with tramadol. They are selective COX-2 inhibitors. The most important of these is the marketed drug celecoxib. Its chemical name is 4-[5-(4-methylphenyl)-3-(trifluoromethyl)-pyrazol-1-yl]benzenesulfonamide. It has an empirical formula of $C_{17}H_{14}F_3N_3O_2S$.

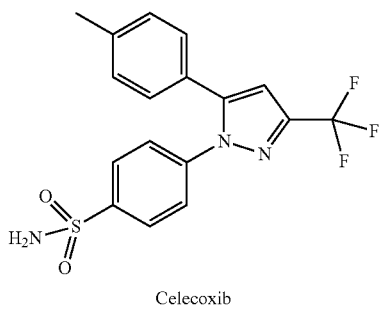 [SMILES: Cc1ccc(-c2cc(C(F)(F)F)nn2-c2ccc(S(N)(=O)=O)cc2)cc1]

Celecoxib

NSAIDs like the coxibs have analgesic activity in a number of pain symptoms. The basis of their activity is inhibition of cyclooxygenase (COX), one of the two activities of prostaglandine endoperoxide synthase (PGHS). It is a key enzyme in the prostaglandin pathway.

"Drugable form (of tramadol)" as used herein is defined as any form (salt, amorphous crystal, solution, dispersion, mixture etc,) that tramadol might take which still can be formulated into a pharmaceutical formulation usable as a medicament to treat a disease or a symptom, especially pain.

"Co-Crystal" as used herein is defined as a crystalline material comprising two or more compounds at ambient temperature (20 to 25° C., preferably 20° C.), of which at least two are held together by weak interaction, wherein at least one of the compounds is a co-crystal former. Weak interaction is being defined as an interaction which is neither ionic nor covalent and includes for example: hydrogen bonds, van der Waals forces, and π-π interactions. Solvates of tramadol that do not further comprise a co-crystal former are not co-crystals according to the present invention. The co-crystals may however, include one or more solvate molecules in the crystalline lattice. Just for the sake of clarity the distinction between crystalline salt and a co-crystal has to be stressed here. An API bound to another compound forming a salt by means of ionic interaction can be considered as one "compound" according to the invention, but it cannot be considered as two compounds by itself.

In scientific literature there currently is some discussion on the proper use of the word co-crystal (see for example Desiraju, Cryst. Eng. Comm., 2003, 5(82), 466-467 and Dunitz, Cryst. Eng. Comm., 2003, 5(91), 506). A recent article by Zawarotko (Zwarotko, Crystal Growth & Design, Vol. 7, No. 1, 2007, 4-9) gives a definition of co-crystal which is in line with the definition given above and thus also is a definition of "co-crystal" according to this invention. According to this article "a co-crystal is a multiple component crystal in which all components are solid under ambient conditions when in their pure form. These components consist of a target molecule or ion and a molecular co-crystal former(s); when in a co-crystal, they coexist at a molecular level within a single crystal".

"Co-crystal former" as used herein is defined as a molecule being an active agent selected from NSAIDs/Coxibs, and with which tramadol is able to form co-crystals.

"Active agents" are APIs which show a pharmaceutical effect and thus can be identified as being pharmaceutically active. In a more narrow sense this definition is encompassing all APIs being marketed or under clinical trial for the treatment of diseases. "Active agents with analgesic activity" are APIs (Active Pharmaceutical Ingredients) which show efficacy in well-known animal models of pain and thus can be identified as being analgesics. In a more narrow sense this definition is encompassing all APIs being marketed or under clinical trial for a labelling including an indication falling under the definition of pain, including also migraine. These indications might include acute pain, chronic pain, neuropathic pain, hyperalgesia, allodynia or cancer pain, including diabetic neuropathy or diabetic peripheral neuropathy, osteoarthritis or fibromyalgia and all their subforms. Examples of "active agents with analgesic activity" include an NSAID like celecoxib or tramadol and its N-desmethyl-metabolite.

"Pain" is defined by the International Association for the Study of Pain (IASP) as "an unpleasant sensory and emotional experience associated with actual or potential tissue damage, or described in terms of such damage (IASP, Classification of chronic pain, $2^{nd}$ Edition, IASP Press (2002), 210). Even though pain is always subjective its causes or syndromes can be classified. One classification to denominate subtypes of pain would be to divide the general pain syndrome into the subtypes of acute and chronic pain or—according to the pain intensity—into mild, moderate and severe pain. In other definitions the general pain syndrome is also divided into "nociceptive" (caused by activation of nociceptors), "neuropathic" (caused by damage to or malfunction of the nervous system) and pain related to central sensitization (central pain syndrome).

According to the IASP "allodynia" is defined as "a pain due to a stimulus which does not normally provoke pain" (IASP, Classification of chronic pain, $2^{nd}$ Edition, IASP Press (2002), 210). Even though the symptoms of allodynia are most likely associated as symptoms of neuropathic pain this is not necessarily the case so that there are symptoms of allodynia not connected to neuropathic pain though rendering allodynia in some areas broader than neuropathic pain.

The IASP further draws the following difference between "allodynia", "hyperalgesia" and "hyperpathia" (IASP, Classification of chronic pain, $2^{nd}$ Edition, IASP Press (2002), 212):

| Allodynia | Lowered threshold | Stimulus and response mode differ |
| --- | --- | --- |
| Hyperalgesia | Increased response | Stimulus and response rate are the same |
| Hyperpathia | Raised threshold; Increased response | Stimulus and response rate may be the same or different |

According to the IASP "neuropathy" is defined as "a primary lesion or dysfunction in the nervous system" (IASP, Classification of chronic pain, $2^{nd}$ Edition, IASP Press (2002), 211). Neuropathic pain may have central or peripheral origin.

"Sciatica" or "sciatic neuritis is defined herein as a set of symptoms including pain that derive from irritation of the sciatic nerve or its roots, "Frozen shoulder" or "adhesive capsulitis" is defined herein as a symptom wherein the connective tissue surrounding the shoulder joint or the shoulder capsule itself, is causing chronic pain, becoming inflamed and stiff.

"Ankylosing spondylitis" or "Morbus Bechterew" is a chronic, inflammatory arthritis and autoimmune disease. It mainly affects joints in the spine and the sacroilium in the pelvis, causing eventual fusion of the spine.

"Pain related to central sensitization"/"central pain syndrome" is defined within this application as a neurological condition caused by damage to or dysfunction of the central nervous system (CNS), which includes the brain, brainstem, and spinal cord. This syndrome can inter alia be caused by stroke, multiple sclerosis, tumors, epilepsy, brain or spinal cord trauma, or Parkinson's disease.

"Nociceptive pain " is defined as a type of pain caused by activation of nociceptors. It can be divided into somatic and visceral pain. "Visceral pain" is pain generally originating from the organs, whereas "(deep) somatic pain" originates from ligaments, tendons, bones, blood vessels, fasciae and muscles.

In one embodiment of the co-crystal according to the invention, the NSAID/s/coxib/s is/are chosen in such a way that if compared to either tramadol alone, or to a mixture of tramadol and the corresponding active agent/s/coxib:
  the solubility of the co-crystal is increased; and/or
  the dose response of the co-crystal is increased; and/or
  the efficacy of the co-crystal is increased; and/or
  the dissolution of the co-crystal is increased; and/or
  the bioavailability of the co-crystal is increased; and/or
  the stability of the co-crystal is increased; and/or
  the hygroscopicity of the co-crystal is decreased; and/or
  the form diversity of the co-crystal is decreased; and/or
  the morphology of the co-crystal is modulated.

"Mixture of tramadol and the corresponding active agent/s" is defined as a mixture of the active agent or agents in question (the NSAID/coxib) with tramadol which is only a physical mixture without any coupling forces between the compounds and thus neither includes salts nor another co-crystal.

In a further embodiment the NSAID being a Coxib is selected from celecoxib, etoricoxib, lumiracoxib, parecoxib, rofecoxib, valdecoxib, and cimicoxib.

In a further embodiment of the co-crystal according to the invention, the NSAID being a coxib is selected from:
  Celecoxib,
  Etoricoxib,
  Lumiracoxib,
  Parecoxib,
  Rofecoxib,
  Valdecoxib, or
  Cimicoxib.

Another very preferred aspect of the invention relates to a co-crystal according to the invention, wherein the NSAID being a coxib is celecoxib or salts thereof.

Another embodiment of the invention relates to a co-crystal according to the invention, wherein the tramadol is (−)-tramadol or (+)-tramadol or salt thereof.

Another embodiment of the invention relates to a co-crystal according to the invention, wherein the tramadol is (rac)-tramadol or salt thereof.

Especially preferred is a pharmaceutical compound comprising tramadol and celecoxib, preferably a pharmaceutical compound comprising (rac)-tramadol•HCl and celecoxib.

As illustrated in more detail below tramadol—and especially the racemate—forms co-crystals with celecoxib. Generally co-crystals obtained have a specific stoichiometry which depends upon the structure of each co-crystal forming NSAID. In this specific case of the co-crystal between (rac)-tramadol and celecoxib being the co-crystal former the molecular ratio between tramadol and celecoxib is 1 to 1.

The term "salt" is to be understood as meaning any form of tramadol or the NSAID/coxib according to the invention in which this assumes an ionic form or is charged and is coupled with a counter-ion (a cation or anion) or is in solution. By this are also to be understood complexes of tramadol or the NSAID/coxib with other molecules and ions, in particular complexes which are complexed via ionic interactions. This also includes physiologically acceptable salt.

The term "solvate" according to this invention is to be understood as meaning any form of the tramadol or NSAID/coxib in which the compound has attached to it via non-covalent binding another molecule (most likely a polar solvent) especially including hydrates and alcohol solvates, e.g. methanol solvate.

In a further preferred embodiment of the invention, co-crystal according to the invention, is selected from
  a co-crystal comprising (rac)-tramadol either as a free base or as a physiologically acceptable salt and celecoxib;
  a co-crystal comprising (+)-tramadol either as a free base or as a physiologically acceptable salt and celecoxib;
  a co-crystal comprising (−)-tramadol either as a free base or as a physiologically acceptable salt and celecoxib; or preferably
  a co-crystal comprising (rac)-tramadol•HCl (the hydrochloride salt of tramadol) and celecoxib.

A highly preferred embodiment of the co-crystals according to the invention the co-crystal is formed from (rac)-tramadol either as a free base or as a physiologically acceptable salt and celecoxib and celecoxib, preferably from (rac)-tramadol•HCl and celecoxib.

In a highly preferred embodiment of these selected co-crystals, the molecular ratio between the (rac)-tramadol•HCl and celecoxib is 1:1.

In a preferred embodiment of a co-crystal with a molecular ratio between (rac)-tramadol•HCl and celecoxib of 1:1 according to the invention, the co-crystal shows a Powder X-Ray Diffraction pattern with peaks [2θ] at 7.1, 9.3, 10.2, 10.7, 13.6, 13.9, 14.1, 15.5, 16.1, 16.2, 16.8, 17.5, 18.0, 19.0, 19.5, 19.9, 20.5, 21.2, 21.3, 21.4, 21.8, 22.1, 22.6, 22.7, 23.6, 24.1, 24.4, 25.2, 26.1, 26.6, 26.8, 27.4, 27.9, 28.1, 29.1, 29.9, 30.1, 31.1, 31.3, 31.7, 32.5, 32.8, 34.4, 35.0, 35.8, 36.2 and 37.2 [°].

The 2θ values were obtained using copper radiation ($Cu_{K\alpha 1}$ 1.54060 Å).

In a preferred embodiment of a co-crystal with a molecular ratio between (rac)-tramadol•HCl and celecoxib of 1:1 according to the invention, the co-crystal shows a Fourier Transform Infra Red pattern with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) cm$^{-1}$.

In a preferred embodiment of a co-crystal with a molecular ratio between (rac)-tramadol•HCl and celecoxib of 1:1 according to the invention, the co-crystal has an orthorhombic unit cell with the following dimensions:

$a=11.0323(7)$ Å

$b=18.1095(12)$ Å

$c=17.3206(12)$ Å

In a preferred embodiment of a co-crystal with a molecular ratio between (rac)-tramadol•HCl and celecoxib of 1:1 according to the invention, the endothermic sharp peak of the co-crystal corresponding to the melting point has an onset at 164° C.

Another embodiment of the present invention relates to a process for the production of a co-crystal according to the invention as described above comprising the steps of:
(a) dissolving or suspending an NSAID—like a coxib—in a solvent; optionally heating the solution or dispersion to a temperature above ambient temperature and below the boiling point of the solution or dispersion;
(b) dissolving together with, or after, or before step (a) tramadol either as a free base or as a salt in a solvent,
(c) adding the solution of (b) to the solution of (a) and mixing them;
(d) cooling the mixed solution/dispersion of step (c) to ambient temperature;
(e) optionally evaporating part or all of the solvent; and
(f) filtering-off the resulting co-crystals.

Another embodiment of the present invention relates to a process for the production of a co-crystal according to the invention as described above comprising the steps of:
(a) dissolving or suspending an NSAID—like a coxib—in a solvent; optionally heating the solution or dispersion to a temperature above ambient temperature and below the boiling point of the solution or dispersion;
(b) dissolving together with, or after, or before step (a) tramadol either as a free base or as a salt in a solvent, optionally combined with step (a) by dissolving tramadol already together with the NSAID—like a coxib—in step (a)
(c) optionally adding the solution of (b) to the solution of (a) and mixing them;
(d) optionally adding a solvent to the solution of (a), (b) or (c) and mixing them;
(e) cooling the mixed solution/dispersion of step (a), (b), (c) or (d) to ambient temperature or below;
(f) optionally evaporating part or all of the solvent; and
(g) filtering-off the resulting co-crystals.

"Ambient temperature" is defined here as a temperature between 20 and 25° C., preferably being 20° C.

The solvents usable in these processes include water or organic solvents, preferably solvents selected from acetone, isobutyl acetate, acetonitrile, ethyl acetate, 2-butanol, dimethylcarbonate, chlorobenzene, butylether, diisopropylether, dimethylformamide, ethanol, water, hexane (also cyclohexane), isopropanol, methyl ethyl ketone (also methyl isobutyl-ketone), methanol, methyl t-butyl ether, 3-pentanone, toluene and 1,1,1-trichloroethane, most preferably including alcohols, like ethanol. It is preferable—but not necessary—that the solvents in steps (a) and (c) are identical.

The molecular ratio between tramadol and the NSAID—like the coxib—lies between 4:1 to 1:4, preferably from 3:1 to 1:3 and more preferably from 1:1 to 1:2.

Preferably the tramadol-solution in step (b) has a concentration of between 3M and 0.01 M.

The parts of the co-crystal according to the invention are well-known drugs with analgesic properties sometimes used for a long time worldwide. Due to this a further object of the present invention is a medicament comprising a co-crystal according to the invention.

Thus the invention also concerns a medicament comprising at least one co-crystal according to the invention as described above and optionally one or more pharmaceutically acceptable excipients.

The invention also relates to a pharmaceutical composition that comprises a therapeutically effective amount of the co-crystal according to the invention in a physiologically acceptable medium.

The association of two active principles in the same crystal exhibits several advantages. Being linked, they often behave as a single chemical entity, thus facilitating the treatments, formulation, dosage etc. In addition to that, with both tramadol and the NSAID—like the coxib—being active analgesics these co-crystals are highly useful in the treatment of pain, especially also not losing any activity/weight by the addition of pharmacologically useless counterions as in salts with no API. In addition the two active principles are complementing each other in the treatment especially of pain, but possibly also of various other diseases or symptoms. Thus, the co-crystals according to the invention do combine a high number of advantages over the state of the art.

Another advantage is that the association of two active principles into one unique species seems to allow for a better Pharmacokinetic/Pharmacodynamic (PKPD) including also a better penetration of the blood-brain barrier, which helps in the treatment of pain.

In general, in most embodiments in which the co-crystals of tramadol are used (e.g. for the treatment of pain etc.), these co-crystals would be formulated into a convenient pharmaceutical formulation or a medicament. Accordingly, a desirable advantage of a co-crystal of tramadol would show improved pharmaceutical properties and features, especially when compared to the free base or tramadol hydrochloride. Thus, the co-crystal of tramadol according to the invention should desirably show at least one, preferably more, of the following features:
- to have a very small particle size, e.g. from 300 μm or lower; or
- to be and/or remain essentially free of agglomerates; or
- to be less or not very hygroscopic; or
- to help in formulating controlled release or immediate release formulations; or
- to have a high chemical stability; or
- if given to a patient
- to decrease the inter- and intra-subject variability in blood levels; or
- to show a good absorption rate (e.g. increases in plasma levels or AUC); or
- to show a high maximum plasma concentration (e.g. $C_{max}$); or to show decreased time to peak drug concentrations in plasma ($t_{max}$); or to show changes in half life of the compound ($t_{1/2}$), in whichever direction this change is preferably directed.

The medicament or pharmaceutical compositions according to the present invention may be in any form suitable for the application to humans and/or animals, preferably humans including infants, children and adults and can be produced by standard procedures known to those skilled in the art. The medicament of the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Typically, the medicaments according to the present invention may contain 1-60% by weight of one or more of the co-crystals as defined herein and 40-99% by weight of one or more auxiliary substances (additives/excipients).

The compositions of the present invention may also be administered topically or via a suppository.

The daily dosage for humans and animals may vary depending on factors that have their basis in the respective species or other factors, such as age, sex, weight or degree of illness and so forth. The daily dosage for humans preferably is in the range of 5 to 500 milligrams of tramadol to be administered during one or several intakes per day.

A further aspect of the invention relates to the use of a co-crystal according to the invention as described above for the treatment of pain, preferably acute pain, chronic pain, neuropathic pain, hyperalgesia, allodynia or cancer pain, including diabetic neuropathy or osteoarthritis or fibromyalgia. The invention thus also relates to the use of a co-crystal according to the invention as described above in the production of a medicament for the treatment of pain, preferably acute pain, chronic pain, neuropathic pain, hyperalgesia, allodynia or cancer pain, including diabetic neuropathy or osteoarthritis or fibromyalgia. A further aspect of the invention relates to the use of a co-crystal according to the invention as described above for the treatment of pain, preferably acute pain, chronic pain, neuropathic pain, severe to moderate pain, hyperalgesia, allodynia or cancer pain, including diabetic neuropathy, osteoarthritis, fibromyalgia; rheumatoid arthritis, ankylosing spondylitis, frozen shoulder or sciatica. The invention thus also relates to the use of a co-crystal according to the invention as described above in the production of a medicament for the treatment of pain, preferably acute pain, chronic pain, neuropathic pain, severe to moderate pain, hyperalgesia, allodynia or cancer pain, including diabetic neuropathy, osteoarthritis, fibromyalgia; rheumatoid arthritis, ankylosing spondylitis, frozen shoulder or sciatica. A further aspect of the invention relates to a co-crystal according to the invention as described above for (use in) the treatment of pain, preferably acute pain, chronic pain, neuropathic pain, hyperalgesia, allodynia or cancer pain, including diabetic neuropathy or osteoarthritis or fibromyalgia. A further aspect of the invention relates to the co-crystal according to the invention as described above for (use in) the treatment of pain, preferably acute pain, chronic pain, neuropathic pain, severe to moderate pain, hyperalgesia, allodynia or cancer pain, including diabetic neuropathy, osteoarthritis, fibromyalgia; rheumatoid arthritis, ankylosing spondylitis, frozen shoulder or sciatica. Preferably these uses are provided for in form of a medicament or a pharmaceutical composition according to the invention as described above.

A further aspect of the invention relates to a co-crystal according to the invention as described above for (use in) the treatment of pain, or preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. A further aspect of the invention relates to the use of a co-crystal according to the invention as described above for the treatment of pain, preferably acute pain, or preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. The invention thus also relates to the use of a co-crystal according to the invention as described above in the production of a medicament for the treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. Preferably these uses are provided for in form of a medicament or a pharmaceutical composition according to the invention as described above.

The uses of a co-crystal according to the invention (described above) or the respective method of treatment (described below) is preferably related to pain, including nociceptive pain (which includes somatic and visceral pain). These preferred embodiments of the invention may also be related to neuropathic pain and/or to pain related to central sensitization (the so-called "central pain syndrome").

The uses of a co-crystal according to the invention (described above) or the respective method of treatment (described below) may preferably also be related to acute and chronic pain.

The uses of a co-crystal according to the invention (described above) or the respective method of treatment (described below) may preferably also be related to mild, to moderate and to severe pain.

Another object of the current invention is a method of treatment of pain, preferably acute pain, chronic pain, neuropathic pain, hyperalgesia, allodynia or cancer pain, including diabetic neuropathy or osteoarthritis or fibromyalgia, by providing to a patient in need thereof a sufficient amount of a co-crystal according to the invention as described above. Another object of the current invention is a method of treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica, by providing to a patient in need thereof a sufficient amount of a co-crystal according to the invention as described above. Preferably the co-crystal according to the invention is provided in physiologically suitable form like e.g. in form of a medicament or a pharmaceutical composition according to the invention as described above.

The present invention is illustrated below with the help of the following figures and examples. These illustrations are given solely by way of example and do not limit the invention.

BRIEF DESCRIPTION OF THE FIGURES

FIG. 8: Comparison of the effects of a co-crystal of (rac)-tramadol•HCl-celecoxib (1:1), of tramadol and of celecoxib on reversal of incision-induced thermal hyperalgesia in the incised rat hind paw following a single dose (8-10 per group). All data are presented as means±SEM.

FIG. 9: Effects of a co-crystal of (rac)-tramadol•HCl-celecoxib (1:1) [the right column in each triplet of bars], of tramadol [the central/middle column in each triplet of bars] and of celecoxib [the left column in each triplet of bars] given intraperitoneally 4.5 h after induction by carrageenan (n=8-10 per dose group), on motor behaviour of monoarthritic rats measured walking across the CBMS 30 min after drugs administration.

EXAMPLES

Example 1: (rac)-tramadol•HCl-celecoxib (1:1) Co-crystal

Figure 1:
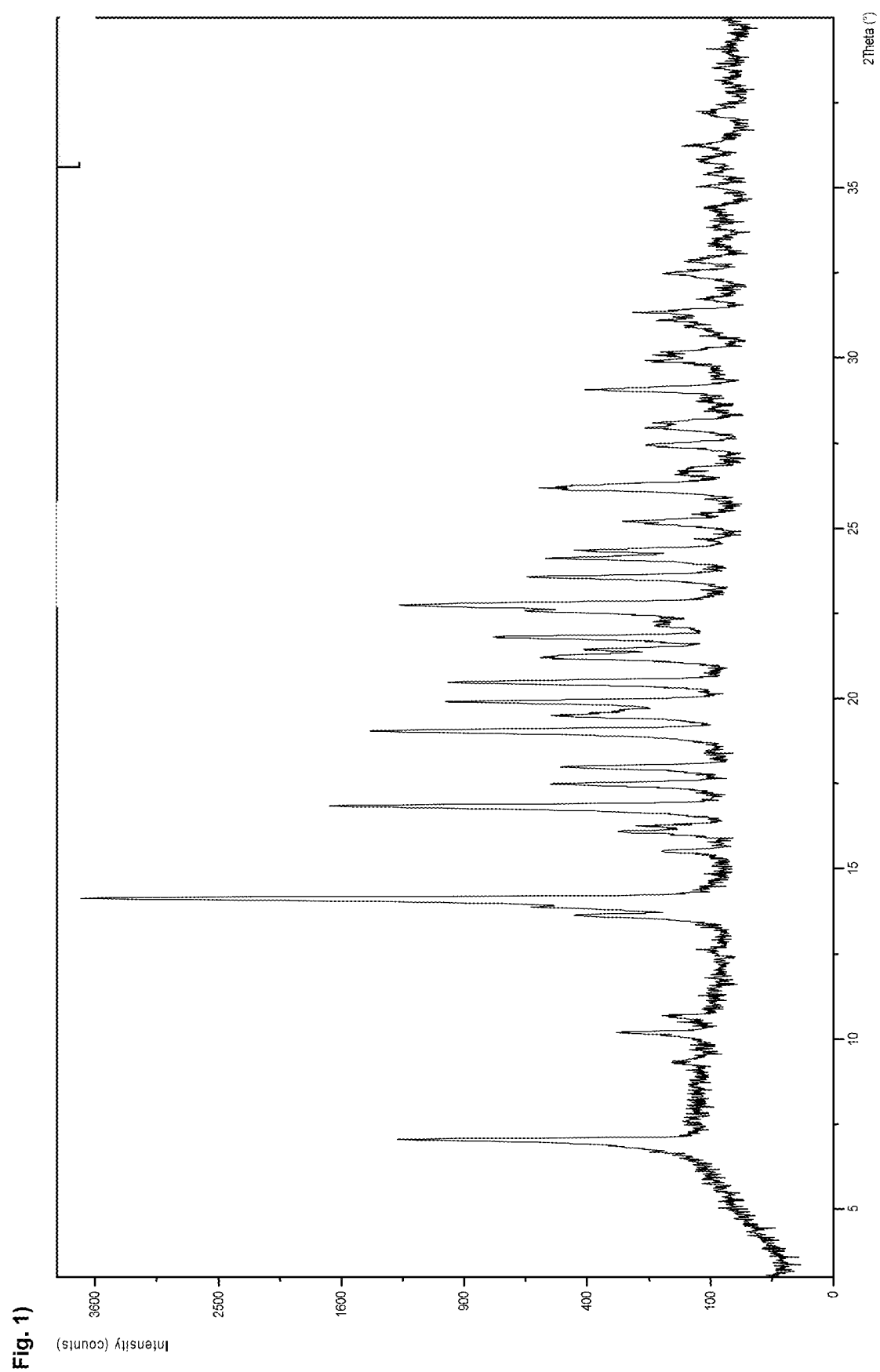
FIG. 1: Powder X-Ray diffraction pattern of the (rac)-tramadol•HCl-celecoxib (1:1) co-crystal.

Processes to Obtain (rac)-tramadol•HCl-celecoxib (1:1) Co-crystal:

Example 1a: (Preparation Via Solvent-Assisted Grinding)

A 5 mL stainless steel ball-mill reactor was charged with two 7 mm steel balls, (rac)-tramadol hydrochloride (48 mg, 0.16 mmol), celecoxib (61 mg, 0.16 mmol, 1 eq) and 1 drop of methyl isobutyl ketone. The reactor was agitated at 30 Hz for 45 minutes. Traces of solvent were removed in vacuo affording (rac)-tramadol•HCl-celecoxib (1:1) co-crystal as a white solid (109 mg, quantitative yield).

Example 1b: (Large Scale Via Crystallization)

To a 1 L three necked flask equipped with mechanical stirrer, addition funnel and cooler containing tramadol•HCl (26.54 g, 88.5 mmol) and celecoxib (33.74 g, 88.5 mmol, 1 eq.), was added 122 mL ethanol. The resultant suspension was heated to reflux (complete dissolution). Cyclohexane (203 mL) was added slowly to the solution maintaining the reflux (addition time 20 min) and then, the solution was cooled slowly to room temperature with stirring. The solution was seeded at 55° C. with form obtained in Example 1a and the crystallization started). The mixture was cooled 2 h at 0° C.

The white solid was filtered with a sintered funnel n° 3 and washed with a solvent mixture at 0-5° C. (1 vol., 60 mL, (0.6:1) EtOH/cyclohexane). After drying 2 days at room temperature under vacuum, (rac)-tramadol•HCl-celecoxib (1:1) co-crystal was obtained as a white solid (54.6 g, 91% yield).

Figure 2:
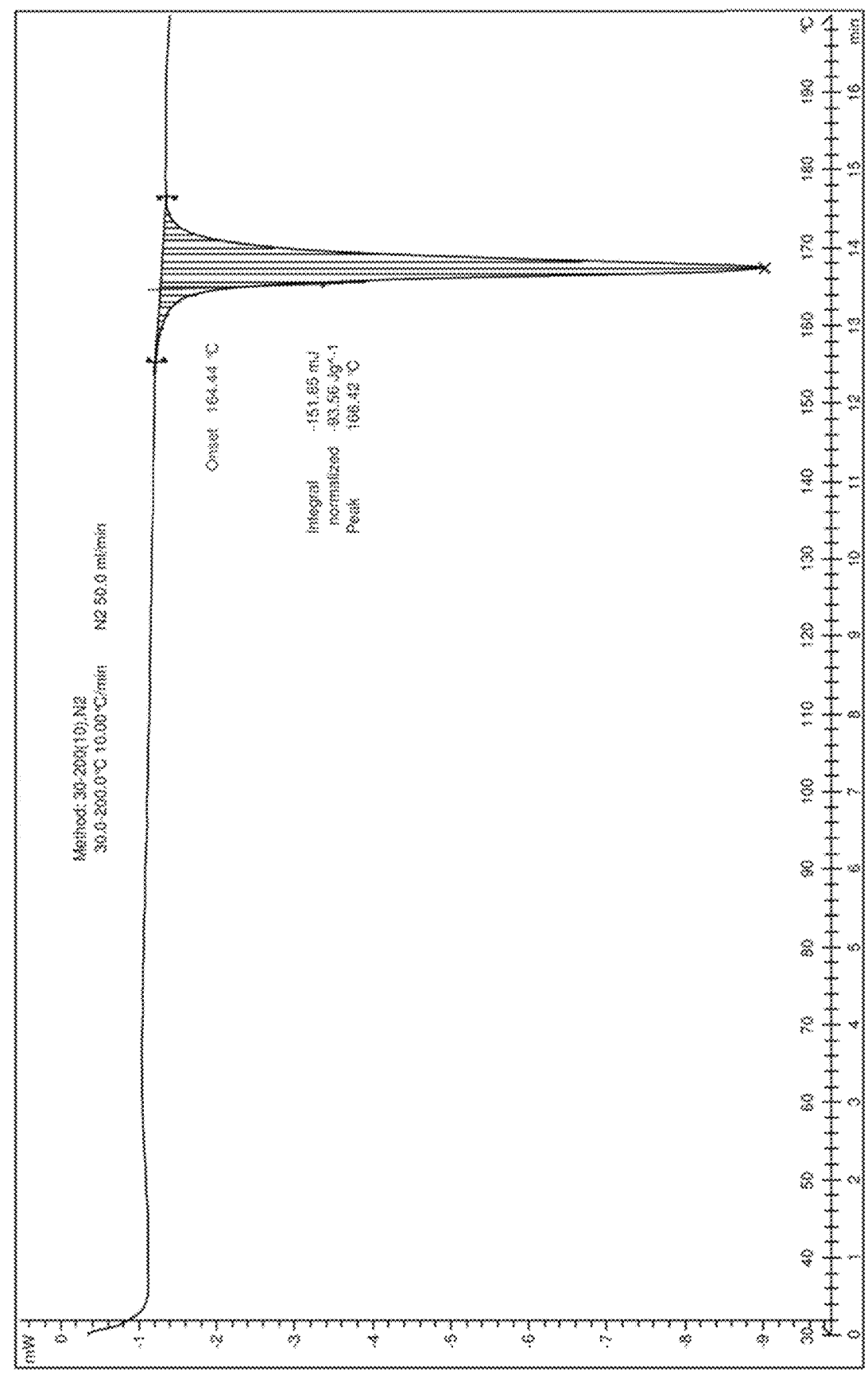
FIG. 2: DSC analysis of the (rac)-tramadol•HCl-celecoxib (1:1) co-crystal.
Figure 3:
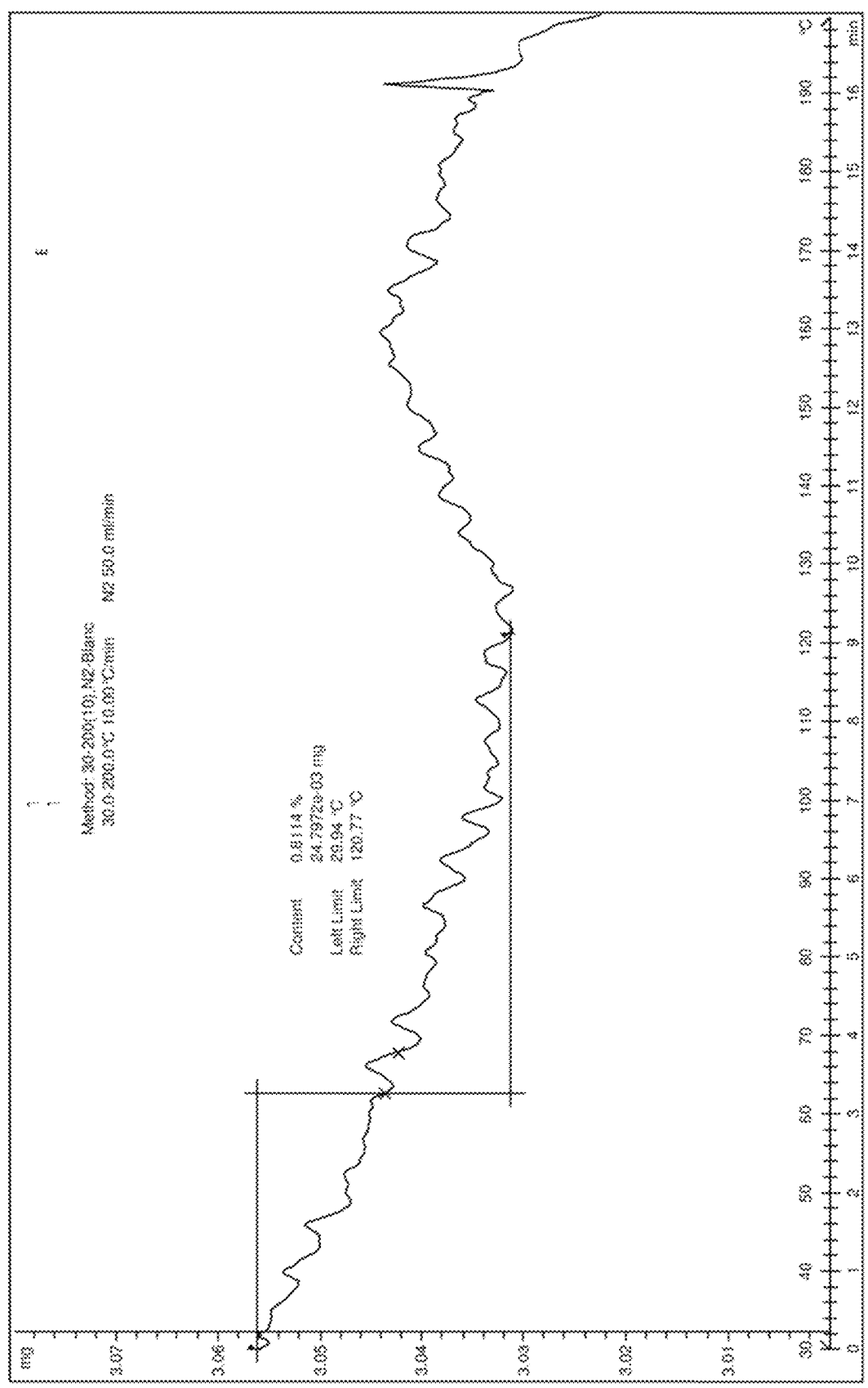
FIG. 3: TG analysis of the (rac)-tramadol•HCl-celecoxib (1:1) co-crystal.

Characterisation of the Co-crystal:

(rac)-Tramadol•HCl-celecoxib (1:1) co-crystal obtained according to example 1 was fully characterised by $^1$H-NMR, FTIR, powder X-Ray diffraction, DSC and TG (see FIGS. 1 to 3).

Powder X-ray Diffraction (PXRD) Pattern of a (rac)-tramadol•HCl-celecoxib (1:1) Co-crystal: (see FIG. 1):

PXRD analysis was performed using a Philips X'Pert diffractometer with Cu $K_\alpha$ radiation in Bragg-Brentano geometry. The system is equipped with a monodimensional, real time multiple strip detector. The measurement parameters were as follows: the range of 2θ was 3° to 40° at a scan rate of 8.8° per minute (see FIG. 1). The peaks expressed in angles 2θ and d-values are described in detail in table 1:

TABLE 1

List of selected peaks obtained by powder X-Ray diffraction of (rac)-tramadol•HCl-celecoxib (1:1) co-crystal.

| Angle 2θ[1] | d-Value (Å) | Relative Intensity % |
|---|---|---|
| 7.06 | 12.52 | 29 |
| 9.32 | 9.49 | 1 |
| 10.21 | 8.67 | 5 |
| 10.69 | 8.27 | 2 |
| 13.64 | 6.49 | 10 |
| 13.86 | 6.39 | 14 |
| 14.13 | 6.27 | 100 |
| 15.53 | 5.71 | 3 |
| 16.10 | 5.51 | 6 |
| 16.25 | 5.45 | 5 |
| 16.85 | 5.26 | 44 |
| 17.50 | 5.07 | 12 |
| 18.00 | 4.93 | 11 |
| 19.05 | 4.66 | 38 |
| 19.48 | 4.56 | 11 |
| 19.91 | 4.46 | 25 |
| 20.48 | 4.34 | 25 |
| 21.18 | 4.19 | 11 |
| 21.27 | 4.18 | 11 |
| 21.44 | 4.14 | 8 |
| 21.80 | 4.08 | 18 |
| 22.14 | 4.02 | 3 |
| 22.56 | 3.94 | 14 |
| 22.73 | 3.91 | 32 |
| 23.57 | 3.78 | 15 |
| 24.11 | 3.69 | 13 |
| 24.36 | 3.65 | 10 |
| 25.20 | 3.53 | 6 |

TABLE 1-continued

List of selected peaks obtained by
powder X-Ray diffraction of (rac)-
tramadol•HCl-celecoxib (1:1) co-crystal.

| Angle 2θ[1] | d-Value (Å) | Relative Intensity % |
|---|---|---|
| 26.12 | 3.41 | 11 |
| 26.58 | 3.35 | 2 |
| 26.77 | 3.33 | 2 |
| 27.45 | 3.25 | 5 |
| 27.94 | 3.19 | 4 |
| 28.13 | 3.17 | 3 |
| 29.07 | 3.07 | 9 |
| 29.91 | 2.99 | 3 |
| 30.15 | 2.96 | 3 |
| 31.11 | 2.88 | 3 |
| 31.34 | 2.85 | 5 |
| 31.74 | 2.82 | 1 |
| 32.49 | 2.76 | 3 |
| 32.83 | 2.73 | 2 |
| 34.42 | 2.61 | 1 |
| 35.04 | 2.56 | 2 |
| 35.76 | 2.51 | 1 |
| 36.24 | 2.48 | 2 |
| 37.19 | 2.42 | 1 |

[1]The 2θ values were obtained using cupper radiation ($Cu_{K\alpha}$ 1.54060 Å)

$^1$H-NMR Spectrum of a Co-Crystal of (Rac)-Tramadol-HCl and Celecoxib (1:1):

Proton nuclear magnetic resonance analyses were recorded in methanol-$d_4$ in a Varian Mercury 400 spectrometer, equipped with a broadband probe ATB 1H/19F/X of 5 mm. Spectra were acquired dissolving 5-10 mg of sample in 0.6 mL of deuterated solvent.

$^1$H NMR spectrum (in d4-methanol at 400 MHz) δ shows peaks at 7.97-7.90 (m, 2H); 7.53-7.46 (m, 2H); 7.30 (t, J=8.0 Hz, 1H); 7.22-7.14 (m, 4H); 7.12-7.09 (m, 1H); 7.07 (d, J=7.8 Hz, 1H); 6.90 (s, 1H); 6.83 (dd, J=2.7 Hz, J=8.2 Hz, 1H); 3.80 (s, 3H); 2.98 (dd, J=9.0 Hz, J=13.3 Hz, 1H); 2.75-2.60 (m, 8H); 2.35 (s, 3H); 2.28-2.18 (m, 1H); 2.00-1.46 (m, 8H) ppm.

FT-IR Spectrum of a Co-crystal of (rac)-tramadol•HCl and Celecoxib (1:1):

FTIR spectra were recorded using a Thermo Nicolet Nexus 870 FT-IR, equipped with a beamsplitter KBr system, a 35 mW He—Ne laser as the excitation source and a DTGS KBr detector. The spectra were acquired in 32 scans at a resolution of 4 cm$^{-1}$.

The sample (KBr pellet) shows a Fourier Transform Infra Red spectrum with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) cm$^{-1}$.

DSC Analysis of a Co-crystal of (rac)-tramadol•HCl and Celecoxib (1:1) (see FIG. 2):

DSC analyses were recorded with a Mettler DSC822$^e$. A sample of 1.6230 mg was weighed into 40 μL aluminium crucible with a pinhole lid and was heated, under nitrogen (50 mL/min), at 10° C./min from 30 to 200° C.

The novel type of crystal of the present invention is characterized in that the endothermic sharp peak corresponding to the melting point has an onset at 164.44° C. (fusion enthalpy—93.56 J/g), measured by DSC analysis (10° C./min) (see FIG. 9).

TG Analysis of a Co-crystal of (rac)-tramadol•HCl and Celecoxib (1:1) (see FIG. 3):

Thermogravimetric analyses were recorded in a thermogravimetric analyzer Mettler TGA/SDTA851$^e$. A sample of 3.0560 mg was weighed into a 70 μL alumina crucible with a pinhole lid and was heated at 10° C./min from 30 to 200° C., under nitrogen (50 mL/min).

The TG analysis of the crystalline form according to the invention shows insignificant weight loss between 30 and 200° C.

Single Crystal XRD Analysis of a Single Crystal of a Co-crystal of (rac)-tramadol•HCl and Celecoxib (1:1) (see FIG. 4):

The crystal structure was determined from single crystal X-ray diffraction data. The colourless prism used (0.33× 0.16×0.11 mm) was obtained from the crystallization of a seeded solution in heptane and IPA of equimolar amounts of (rac)-tramadol hydrochloride and celecoxib.

Analysis was performed at room temperature using a Bruker Smart Apex diffractometer with graphite monochromated Mo $K_\alpha$ radiation equipped with a CCD detector. Data were collected using phi and omega scans (program used: SMART 5.6). No significant decay of standard intensities was observed. Data reduction (Lorentz and polarization corrections) and absorption correction were applied (program used: SAINT 5.0).

The structure was solved with direct methods and least-squares refinement of $F_o^2$ against all measured intensities was carried out (program used: SHELXTL-NT 6.1). All non-hydrogen atoms were refined with anisotropic displacement parameters. Crystal data and structure refinement for (rac)-tramadol-celecoxib (1:1) co-crystal is given in the following table 2.

TABLE 2

Most relevant structural data of the
SCXRD analysis of a co-crystal of
(rac)-tramadol•HCl
celecoxib (1:1)

| Crystal system | Orthorhombic |
|---|---|
| Space group | $Pna2_1$ |
| a (Å) | 11.0323(7) |
| b (Å) | 18.1095(12) |
| c (Å) | 17.3206(12) |
| Volume (Å$^3$) | 3460.5(4) |
| Z | 4 |
| D calc. (Mg/m$^3$) | 1.308 |
| N. of refl. | 8336 |
| Refl. with I > 2σ(I) | 5240 |
| R (I > 2σ(I)) | 0.0584 |

Figure 4:
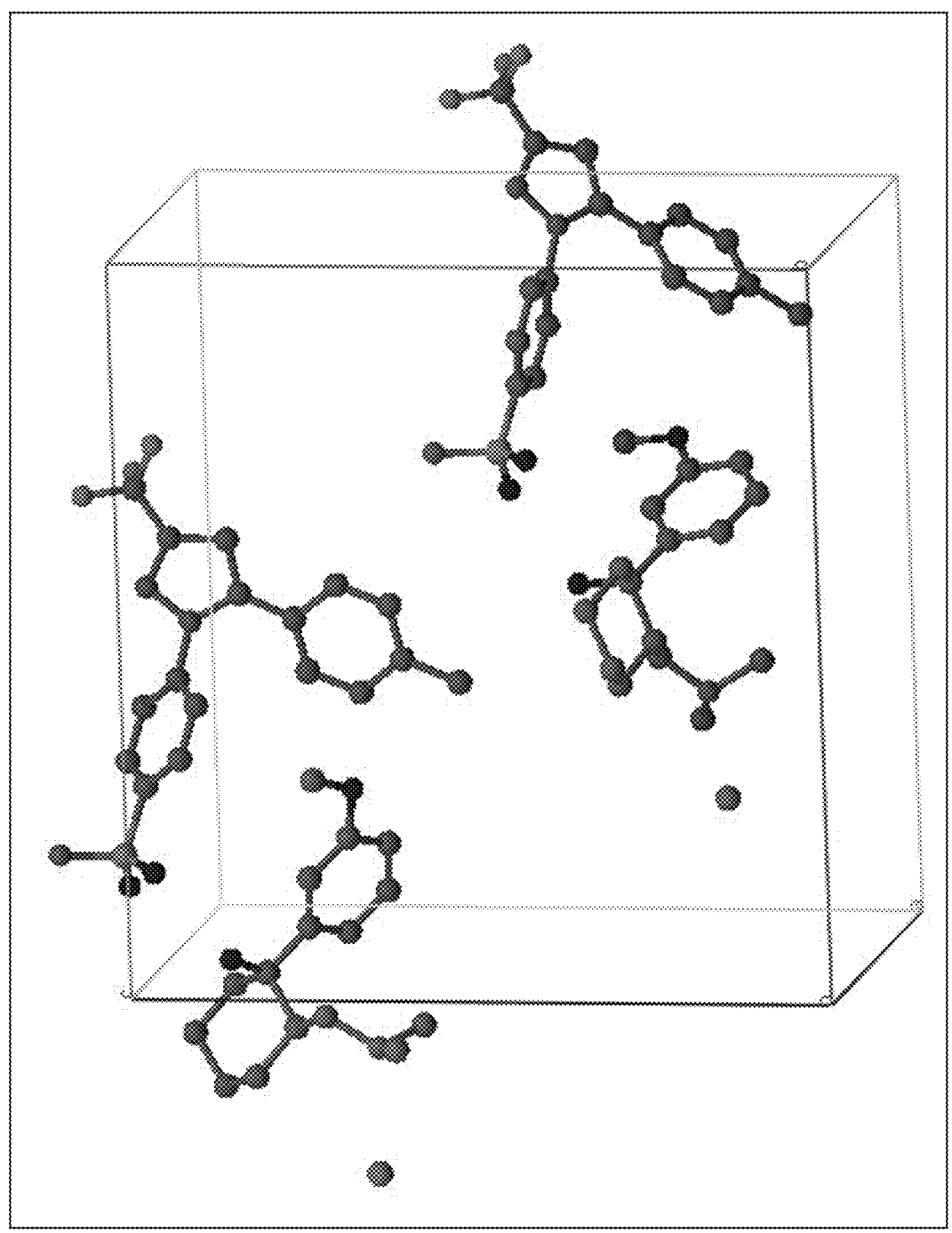
FIG. 4: Structure of the unit cell of the (rac)-tramadol•HCl-celecoxib (1:1) co-crystal obtained by SCXRD analysis showing two molecules of celecoxib and two molecules of tramadol.

The crystal structure is depicted in FIG. 4 (only half of the unitcell contents is shown, hydrogen atoms have been omitted for clarity; program used: Mercury 2.2, C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst., 41, 2008, 466-470).

Simulation of XRPD diffractogram from single crystal data gives an almost identical diagram to the experimental one presented above.

Example 1c: Determination of the Bioavailability of Co-crystal of (rac)-tramadol•HCl-celecoxib (1:1) (Dogs)

The objective was to measure plasma exposure of (rac)-tramadol•HCl and celecoxib in dogs by means of AUC determination of the co-crystal of (rac)-tramadol•HCl-celecoxib (1:1) of the present invention, and comparing it with each active principle of the co-crystal and the fixed combination of the two active principles.

Bioavailability of (rac)-tramadol•HCl-celecoxib co-crystal was compared to those obtained after administration of (rac)-tramadol•HCl plus celecoxib, combined and separately, to beagle dogs (3 males and 3 females) by oral route. Products with an equivalent particle size were orally administered by means of capsules at a dose level of 10 mg/kg of co-crystal (as base) and at an equivalent dose level of comparators (4.1 mg tramadol/kg, 5.9 mg celecoxib/kg). Blood from the dogs was extracted at the following time points: predose, 15 and 30 min; 1, 1.5, 2, 2.5, 3, 3.5, 4, 4.5, 5, 6, 8 and 24 h. The plasma was isolated by centrifugation, purified by SPE and plasma levels were determined by LC-MS-MS. Pharmacokinetic parameters were calculated using non-compartmental pharmacokinetic analysis.

Figure 5:
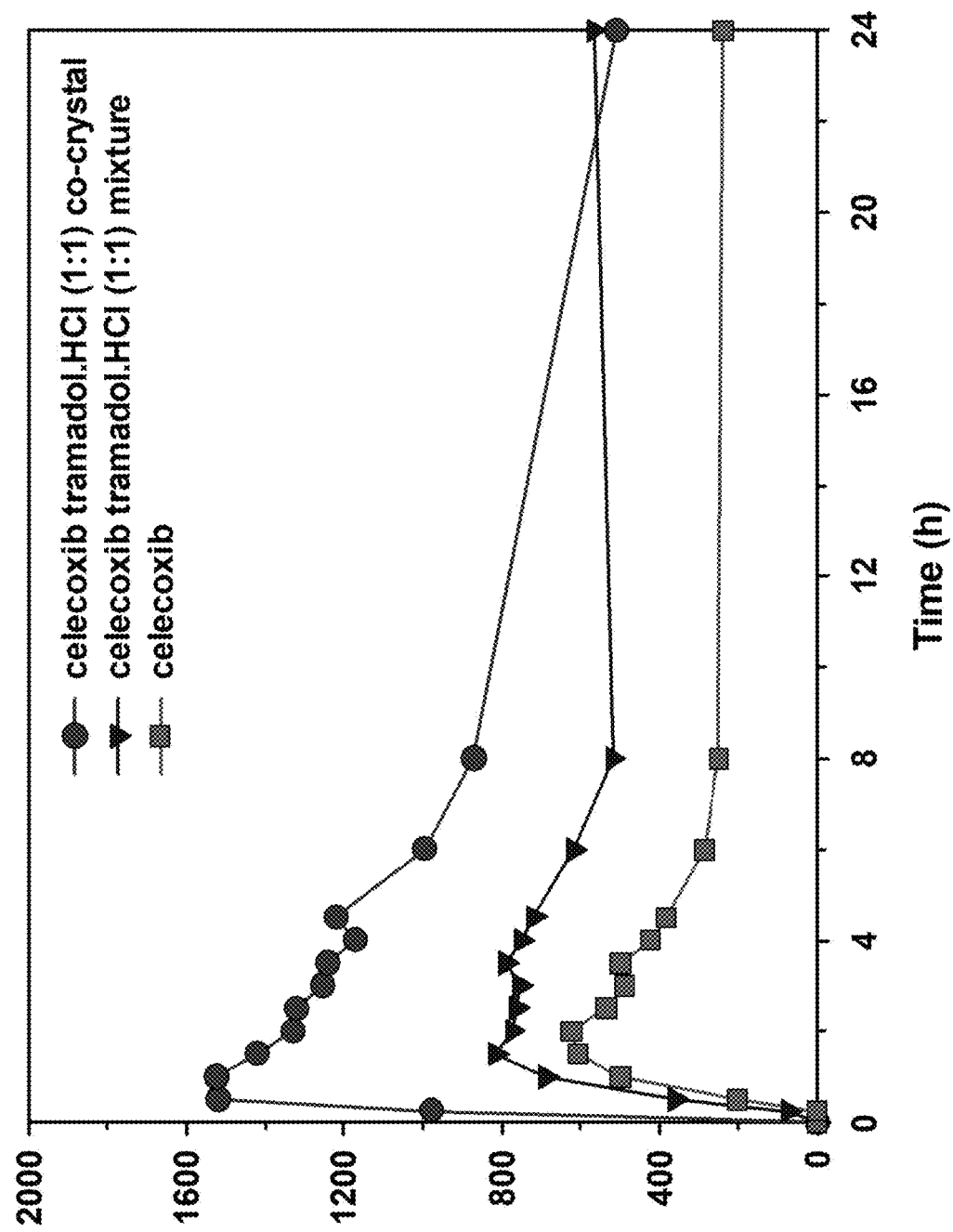
FIG. 5: Showing bioavailability of a co-crystal of (rac)-tramadol•HCl-celecoxib (1:1) in dogs compared to celecoxib alone and to the combination of both API's (the mixture of tramadol and celecoxib).

The results showed an increase exposure of celecoxib when the co-crystal (rac)-tramadol•HCl-celecoxib was administered compared to celecoxib alone and to the combination of both API's (the mixture of tramadol and celecoxib) (see FIG. 5).

Example 1d: Effects on Mechanical Allodynia and Thermal Hyperalgesia in a Postoperative Pain Model in Rat The aim of this study was to evaluate the analgesic efficacy and potency of co-crystal of (rac)-tramadol•HCl-celecoxib (1:1), tramadol and celecoxib in a rat model of postoperative pain after paw incision. Following plantar incision, rats show decreases in response thresholds to temperature (thermal hypersensitivity) and graded von Frey filaments (mechanical hypersensitivity) (Brennan et al., Pain 1996, 64, 493).

To assess the reliability of the efficacy and potency of the compounds tested, two different behavioural assays have been used: tactile allodynia using up and down paradigm by von Frey filaments and thermal hyperalgesia using the plantar test assay (Hargreaves et al., Pain 1988, 32, 77).

Experimental Design:
Animals
Male, Wistar rats (120-160 g, Harlan, Italy) were housed in a climate-controlled room for at least 5 days prior to testing. Food and water were available ad libitum up to test time.

Animal Dosing
The rats were all dosed intraperitoneally with co-crystal of (rac)-tramadol•HCl-celecoxib (1:1) or each agent separately, dissolved in a suspension of 0.5% hydroxypropyl methylcellulose in distilled water. The dosing volume was 10 ml/kg. The antihyperalgesic or antiallodynic response of the animal was subsequently evaluated 60 min after drug administration.

Surgery
Rats were anaesthetized with 3% isofluorane for veterinary use, employing an Ohmeda vaporizer and an anaesthesia chamber. Anaesthesia was kept during the surgical operation by a tube which directs the isoflurane vapours to the animal's snout. Once the rats were anaesthetised, they were laid down in a prone position and their right hindpaws were cleaned out with alcohol. Then, a 1 cm longitudinal incision was made with a number 23 scalpel, through skin and fascia of the plantar aspect of the paw, starting 0.5 cm from the proximal edge of the heel and extending toward the toes. Therefore, both superficial (skin) and deep (muscle) tissues and nerves were injured. Finally, the skin of the paw was stitched with a suturing stitch with breaded silk (3.0) and the wound was cleaned out with povidone.

Assessment of Analgesic Activity in Post-Operative Pain in Rats
The drugs were tested 4 hours after the surgery (plantar incision); 60 minutes after the administration of the product, two behavioural endpoints were evaluated: thermal hypersensitivity or hyperalgesia, and mechanical hypersensitivity or allodynia.

Assessment of Thermal Hypersensitivity (Hyperalgesia) in Post-Operative Pain in Rats
Hypersensitivity or hyperalgesia was assessed by measurement of a response to a thermal stimulus using a Hargreaves apparatus (Ugo Basile plantar test) which selectively elevates the temperature of an individual paw (Dirig, et al., J Neurosci Methods, 1997, 76, 183). Animals were placed in the methacrylate cages of said apparatus, having a crystal floor. The acclimation period within the cages was about 10 minutes. The thermal stimulus came from a lamp moving below the crystal floor and which was applied to both paws, with a minimum interval of 1 minute between both stimulations in order to avoid learning behaviours. The rat is able to withdraw the paw freely when it feels discomfort (pain) produced by the heat coming from the lamp; then it is switched off and the latency time to the withdrawal response is recorded in seconds. In order to avoid hurting the animal's paw, the lamp was automatically switched off after 32 seconds. Hyperalgesia is defined as a reduced latency to response compared to the latency of a vehicle treated animal, and the analgesic effect of the test compound is seen as a (partial) restoration of the latency toward normal (Dirig, et al., J. Pharmacol Expt Therap. 1998, 285, 1031).

Assessment of Mechanical Hypersensitivity (Allodynia) in Post-Operative Pain in Rats
Mechanical allodynia was tested using von Frey filaments. Animals were placed in methacrylate cylinders on an elevated surface, with metallic mesh floor perforated in order to apply the filaments. After an acclimation period of about 30 minutes within the cylinders, both hindpaws were stimulated (the injured and the non-injured paw, serving the latter as control), starting with the lowest force filament (0.4 g) and reaching up to a 15 g filament. The animal's response to pain was manifested by the withdrawal of the paw as a consequence of the painful stimulus caused by a filament. The pressure (force in grams) threshold eliciting the withdrawal of the paw was recorded. The analgesic effect of the test compound is seen as a (partial) restoration of the threshold toward normal.

Analysis of Synergistic Effect
The synergistic interaction between tramadol and celecoxib was determined by isobologram analysis as discloses by R. J. Tallarida, et al., Life Sci., 1989, 45, 947. This procedure involves the determination of the total amount in the mixture that is required to produce a specified synergistic anti-hyperalgesic effect at the 50% dose level (that is, the $ED_{50}$ or Zmix) and the corresponding total amount that would be expected under simple additivity ($ED_{50}$ add or Zadd). Where it is established that Zmix<Zadd for a specific fixed-ratio, then that composition has a synergistic anti-hyperalgesic effect. Both $ED_{50}$ mix and $ED_{50}$ add values are random variables. $ED_{50}$ mix is determined from the dose-response curve for a specific fixed-ratio of the components; $ED_{50}$ add is calculated from the $ED_{50}$ values for the individual drugs. Zmix is then compared to Zadd via a Student's t-test.

Results:

In this study, a dose response of co-crystal of (rac)-tramadol•HCl-celecoxib (1:1), tramadol and celecoxib (intraperitoneal route) were obtained. Mechanical allodynia and thermal hypersensitivity were used as behavioural endpoint. All drugs induced full efficacy when mechanical allodynia was evaluated.

Figure 6:
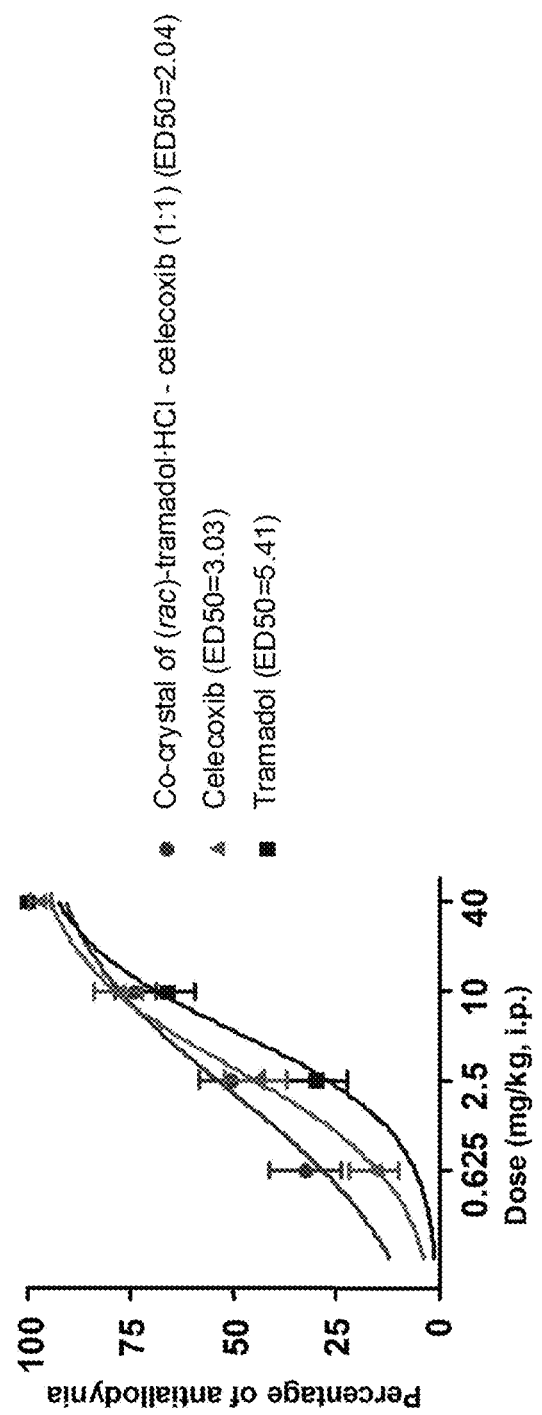
FIG. 6: Comparison of the effects of a co-crystal of (rac)-tramadol•HCl-celecoxib (1:1), of tramadol and of celecoxib on reversal of incision-induced mechanical allodynia in the incised rat hind paw following a single dose (8-10 per group). All data are presented as means±SEM.
Figure 7:
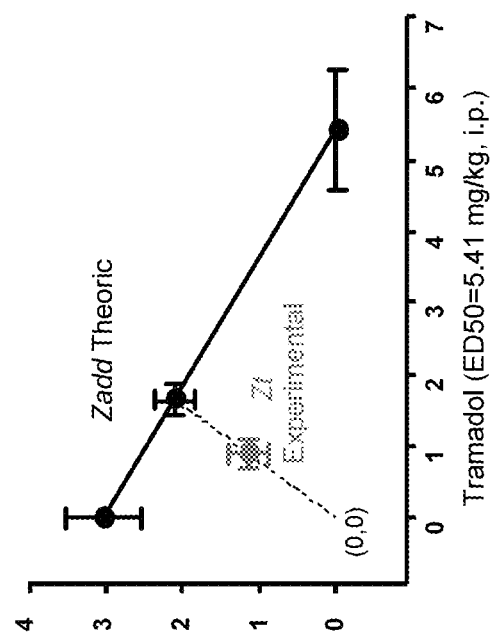
FIG. 7: Isobologram showing anti-allodynic interaction of celecoxib ($ED_{50}$=3.01 mg/kg) and tramadol ($ED_{50}$=5.28 mg/kg) on mechanical allodynia in the paw incision post-operative pain model in rats. The oblique line between x- and y axis is the theoretical additive line. The point in the middle of this line is the theoretical additive point calculated from separate $ED_{50}$. Red: the experimental point (co-crystal of (rac)-tramadol•HCl-celecoxib (1:1) ED50, molecular weight ratio 1:1.27) lies far below the theoretical ED50 (blue), indicating a significant (P<0.05) synergistic interaction.

Results obtained on the effect in mechanical allodynia for co-crystal of (rac)-tramadol•HCl-celecoxib (1:1), tramadol and celecoxib expressed as $ED_{50}$ are shown in Table 3 and FIG. 6, whereas FIG. 7 shows an isobologram of anti-allodynic interaction of celecoxib ($ED_{50}$=3.01 mg/kg) and tramadol ($ED_{50}$=5.28 mg/kg) on mechanical allodynia in this post-surgical pain model. FIG. 8 shows results obtained on the effect of co-crystal of (rac)-tramadol•HCl-celecoxib (1:1), tramadol and celecoxib expressed as ED50 in the incision-induced thermal hyperalgesia in the rat hind paw. Co-crystal of (rac)-tramadol•HCl-celecoxib (1:1) was more potent than tramadol and celecoxib.

TABLE 3

ED50 (mg/kg) of each drug tested obtained after sigmoidal adjustment for mechanical allodynia and thermal hyperalgesia in a model of postoperative pain after paw incision in rats.

| | | ED-50 | | |
|---|---|---|---|---|
| | | Celecoxib | Tramadol | Co-Crystal |
| Behavioural endpoint | Mechanical allodynia | 3.03 | 5.41 | 2.04 |
| | Thermal hyperalgesia | 2.35* | 8.3 | 2.26 |

*Emax 47.53%

The isobologram of FIG. 7 is showing anti-allodynic interaction of celecoxib ($ED_{50}$=3.01 mg/kg) and tramadol ($ED_{50}$=5.28 mg/kg) on mechanical allodynia in the paw incision postoperative pain model in rats. The oblique line between x- and y axis is the theoretical additive line. The point in the middle of this line is the theoretical additive point calculated from separate $ED_{50}$. Grey: the experimental point (co-crystal of (rac)-tramadol•HCl-celecoxib (1:1) $ED_{50}$, molecular weight ratio 1:1.27) lies far below the theoretical $ED_{50}$ (black), indicating a significant (P<0.05) synergistic interaction.

As shown in FIG. 8 tramadol and co-crystal of (rac)-tramadol•HCl-celecoxib (1:1) similarly showed full efficacy when thermal hyperalgesia was used although celecoxib induced only a partial response (Emax: 45%). Clearly co-crystal of (rac)-tramadol•HCl-celecoxib (1:1) was more potent than tramadol ($ED_{50}$ Tram: 8.3 mg/kg vs $ED_{50}$ co-crystal of (rac)-tramadol•HCl-celecoxib (1:1): 2.26 mg/kg) in this parameter suggesting a clear synergistic effect. Isobologram analysis for this behavioural endpoint was not suitable because the ceiling effect of celecoxib (45%).

Conclusion

Co-crystal of (rac)-tramadol•HCl-celecoxib (1:1) administrated intraperitoneal act synergistically to inhibit both mechanical allodynia and thermal hyperalgesia in the paw incision postoperative pain model Example 1e: Effects on Mechanical Allodynia and Movement-Evoked Pain in an Acute Monoarthritic Model in Rat In this study the effects of co-crystal of (rac)-tramadol•HCl-celecoxib (1:1), tramadol and celecoxib on mechanical allodynia and movement-evoked pain were evaluated in an acute monoarthritic rat model. Movement-evoked pain was evaluated by a computerized behavioral monitoring system (CBMS). The use of this method to assess a pain-induced gait adaptation together with the von Frey methodology to evaluate evoked-pain produces a better and more reliable picture of the animal's pain experience.

The rat carrageenan model utilizes inflammation-associated pain following injection of the knee joint (monoarthritic model). The aim of this study was to evaluate the analgesic efficacy and potency of tramadol, celecoxib and co-crystal of (rac)-tramadol•HCl-celecoxib (1:1) in reducing pain behaviour in monoarthritic rats induced by an injection of 300 μg of carrageenan into the right knee joint. The CBMS was used to assess gait related changes 5 hours after carrageenan injection and 30 min after drugs administration. Gait deficits were observed in different CBMS parameters grouped in: statics (print area, print length, print width), dynamics (stand, swing), and coordination (phase dispersion). Mechanical allodynia was measured with von Frey filaments 15 minutes after CBMS gait analysis. In this study, the effects of co-crystal of (rac)-tramadol•HCl-celecoxib (1:1), tramadol and celecoxib were evaluated due to their common prescription for moderate to severe pain associated with injury or inflammation in the clinic.

Experimental Design:

Animals

Male, Wistar rats (225-250 g, Charles River Laboratories) were housed in a climate-controlled room. Food and water were available ad libitum up to test time.

Animal Dosing

Rats were all dosed intraperitoneally with co-crystal of (rac)-tramadol•HCl-celecoxib (1:1) or each agent tramadol hydrochloride and celecoxib separately, dissolved in a suspension of 0.5% hydroxypropyl methylcellulose in distilled water. The dosing volume was 2 ml/kg. The drug response of the animal was subsequently evaluated 30 and 45 min after drug administration (for CBMS and von Frey respectively).

Knee Joint Monoarthritis Induced by Intraarticular Injection of Carrageenan.

Joint inflammation was induced by carrageenan (Sigma Chemical, St. Louis, Mo.) injected percutaneously using a 30-gauge needle through the infrapatellar ligament into the right knee joint cavity (300 μg, 40 μl) with the animal under brief isoflurane (IsoFlo®, Abbott-Esteve, Barcelona, Spain) anaesthesia (3%).

Assessment of Pain-Induced Gait Adaptation with CBMS Method.

Detailed analysis of gait was performed on walking rats using the CBMS method. Briefly, light from a fluorescent tube is sent through a glass plate. Light rays are completely reflected internally. As soon as anything, e.g. a rat's paw, is in contact with the glass surface, light is reflected downwards. It results in a sharp image of a bright paw print. The whole run is recorded via a camera placed under the glass plate.

In the present study, parameters related to single paws were analyzed:

Print Area (expressed in $mm^2$): This parameter describes the total floor area contacted by the paw during the stance phase.

Max Contact Area (expressed in $mm^2$): The maximal contact area describes the paw area contacted at the moment of maximal paw-floor contact, during stance.

Print Width (expressed in mm): It is a measure of the width of the print area.

Print Length (expressed in mm): It is a measure of the length of the print area.

Stand (expressed in s): It is the duration in seconds of contact of a paw with the glass plate.

Swing (expressed in s): It is the duration in seconds of no contact of a paw with the glass plate.

Swing Speed (expressed in m/s): It is the speed (Distance Unit/second) of the paw during Swing. This parameter is computed from stride length and swing duration.

Duty cycle (%): It expresses Stand as a percentage of Step Cycle.

Stand Index: It is a measure for the speed at which the paw loses contact with the glass plate.

Max Contact at (expressed in seconds): It is the time in seconds since the start of the run that a paw makes maximum contact with the glass plate. It can be regarded as the point at which the braking phase turns into the propulsion phase during Stand.

Assessment of Mechanical Hypersensitivity (Allodynia) in Monoarthritic Rats.

Mechanical allodynia was tested using von Frey filaments: Animals were placed in methacrylate cylinders on an elevated surface, with metallic mesh floor perforated in order to apply the filaments. After an acclimation period of about 15 minutes within the cylinders, both hindpaws were stimulated (the injured and the non-injured paw, serving the latter as control), starting with the lowest force filament (0.4 g) and reaching a 15 g filament. The animal's response to pain was manifested by the withdrawal of the paw as a consequence of the painful stimulus caused by a filament. The pressure (force in grams) threshold eliciting the withdrawal of the paw was recorded. The analgesic effect of the test compound is seen as a (partial) restoration of the threshold toward normal.

Results:

Arthritis caused by injection of carrageenan (CAR) into an ankle joint caused a change in several parameters describing the way rats walk, indicating an unwillingness to use the injected paw. CAR-induced gait changes were inhibited by celecoxib, tramadol and co-crystal of (rac)-tramadol•HCl-celecoxib (1:1) (FIG. 9).

The results showed that co-crystal of (rac)-tramadol•HCl-celecoxib (1:1) administration produced greater beneficial effects (relative to the individual administration of tramadol and celecoxib) in various CBMS-associated parameters including: print area, print length, maximal contact area, stand index, and phase dispersion.

FIG. 9 shows the effects of a co-crystal of (rac)-tramadol•HCl-celecoxib (1:1) [the right column in each triplet of bars], of tramadol [the central/middle column in each triplet of bars] and of celecoxib [the left column in each triplet of bars] given intraperitoneally 4.5 h after induction by carrageenan (n=8-10 per dose group), on motor behaviour of monoarthritic rats measured walking across the CBMS 30 min after drugs administration. As outlined above the co-crystal was given at the dose of 20 mg/kg and (rac)-tramadol•HCl or celecoxib given alone at the dose corresponding to which it is present in the co-crystal. Print Area (expressed in mm$^2$) describes the total floor area contacted by the paw during the stance phase. Max Contact Area describes the paw area contacted at the moment of maximal paw-floor contact, during stance. Print Length is a measure of the length of the print area. Stand is the duration in seconds of contact of a paw with the glass plate. Stand Index is a measure for the speed at which the paw loses contact with the glass plate. Swing Speed is the speed (Distance Unit/second) of the paw during Swing. This parameter is computed from stride length and swing duration. Max Contact at is the time in seconds since the start of the run that a paw makes maximum contact with the glass plate. It can be regarded as the point at which the braking phase turns into the propulsion phase during Stand. Phase Dispersion Girdle is a parameter about interlimb coordination using the timed relationships between footfalls of two different paws. All data are presented as means±SEM. * $p<0.05$ co-crystal of (rac)-tramadol•HCl-celecoxib (1:1) vs Tramadol; # $p<0.05$ co-crystal of (rac)-tramadol•HCl-celecoxib (1:1) vs Celecoxib.

Conclusion

Co-crystal of (rac)-tramadol•HCl-celecoxib (1:1) produced a superior benefit over the single drugs tested in various pain-induced gait changes in a rat model of acute monoarthritic pain.

The invention claimed is:

1. A method of treatment of pain comprising administering to a patient in need thereof an effective amount of a co-crystal comprising (rac)-tramadol•HCl and celecoxib.

2. The method according to claim 1, characterized in that the pain to be treated is severe to moderate pain.

3. The method according to claim 1, characterized in that the molecular ratio between the (rac)-tramadol•HCl and celecoxib is 1:1.

4. The method according to claim 1, characterized in that the molecular ratio between the (rac)-tramadol•HCl and celecoxib is 1:1 and that the pain to be treated is severe to moderate pain.

5. The method according to claim 1, comprising administering (rac)-tramadol•HCl and celecoxib in a molecular ratio of 1:1, characterized in that it has an orthorhombic unit cell with the following dimensions:

$a=11.0323(7)$ Å

$b=18.1095(12)$ Å

$c=17.3206(12)$ Å.

6. The method according to claim 1, comprising administering (rac)-tramadol•HCl and celecoxib in a molecular ratio of 1:1, characterized in that it has an orthorhombic unit cell with the following dimensions:

$a=11.0323(7)$ Å

$b=18.1095(12)$ Å

$c=17.3206(12)$ Å;

and that the pain to be treated is severe to moderate pain.

* * * * *

UNITED STATES PATENT AND TRADEMARK OFFICE
CERTIFICATE OF CORRECTION

| | | |
|---|---|---|
| PATENT NO. | : 11,478,488 B2 | |
| APPLICATION NO. | : 16/720574 | |
| DATED | : October 25, 2022 | |
| INVENTOR(S) | : Carlos-Ramón Plata-Salaman and Nicolas Tesson | |

It is certified that error appears in the above-identified patent and that said Letters Patent is hereby corrected as shown below:

On the Title Page

Page 2, Item (56) OTHER PUBLICATIONS:
Column 2, reference "Ofoegbu", Line 24 "Cure" should read -- Curr --.

Signed and Sealed this
Twentieth Day of December, 2022

Katherine Kelly Vidal
*Director of the United States Patent and Trademark Office*